United States Patent [19]

Stowell et al.

[11] 4,010,089

[45] Mar. 1, 1977

[54] REACTING COAL

[75] Inventors: William R. Stowell; Joseph R. Sagmuller, both of Columbus, Ohio

[73] Assignee: Battelle Memorial Institute, Columbus, Ohio

[22] Filed: June 7, 1974

[21] Appl. No.: 477,256

[52] U.S. Cl. .............................. 204/168; 204/170; 204/171; 208/8; 250/542; 250/545
[51] Int. Cl.² ...................... B01K 1/00; C07C 3/24; C10G 1/00
[58] Field of Search .................. 204/168, 170, 171; 208/8

[56] References Cited
UNITED STATES PATENTS

| | | | |
|---|---|---|---|
| 2,074,530 | 3/1937 | Baumann et al. ................. | 204/171 |
| 3,073,769 | 1/1963 | Doukas ............................. | 204/171 |
| 3,384,467 | 5/1968 | Ammann et al. ................. | 48/65 |
| 3,404,078 | 10/1968 | Goldberger ....................... | 204/164 |
| 3,445,191 | 5/1969 | Bruning et al. ................... | 23/277 |
| 3,870,611 | 3/1975 | Vestal ............................... | 204/168 |

*Primary Examiner*—F.C. Edmundson
*Attorney, Agent, or Firm*—Philip M. Dunson

[57] ABSTRACT

Apparatus and method for reacting coal with hydrogen to provide hydrocarbon products. In a container having an anode and a cathode spaced therefrom, an electric potential about 200 to 1000 volts more positive than the potential at the cathode is applied to the anode to provide an electric arc at a current density of about 0.01 to 100 amperes per square centimeter in a reaction zone between them comprising hydrogen at a pressure of about 10 to 500 millimeters of mercury, and thus to maintain a plasma therein. A magnetic field of about 100 to 1000 gauss is provided approximately perpendicular to the arc. Hydrogen is directed into contact with the anode (as through passages therein) and from there into the reaction zone to ionize a substantial portion of the hydrogen positively, while coal is directed either in a slurry or as a fine powder, into contact with the cathode (as through passages therein) and from there into the reaction zone to charge a substantial portion of the coal with a negative potential. The materials as ionized are reacted, whereby the free energy decrease for each reaction at a given temperature is greater than that for molecular hydrogen, and the hydrocarbon products are withdrawn from the reaction zone. The potential difference, current density, pressure, and magnetic field intensity are maintained at values such as to provide a temperature of about 500 to 6000° K in the reaction zone.

9 Claims, 4 Drawing Figures

REACTING COAL

BACKGROUND

This invention relates to the chemical processing of coal by utilizing gaseous plasmas. The final products of this processing are organic gases and compounds. The present invention is especially useful to produce high BTU gas such as methane, ethane, ethylene, and propene, for general purpose use at costs lower than those currently required for such gas production, and to produce acetylene, olefins, and other hydrocarbons at low costs.

In recent years, a great deal of work has been devoted to utilizing plasmas in chemical reactions. The utilization of plasmas to produce acetylenes from coal has been attempted. The techniques which have been tried include the use of microwave plasma discharges of hydrogen, radio frequency plasma discharges of hydrogen, and arc discharges of hydrogen to promote a reaction between the hydrogen gas and coal. The reason for utilizing a plasma lies with the high degree of reactivity which is associated with certain hydrogen species that are found in plasmas of hydrogen. In general, the techniques which have been used require elaborate equipment and too much power input in terms of the electrical power required to generate the plasma to justify a process scale-up to an industrial application.

A method of plasma processing which has been used to produce acetylene has been developed under the direction of Dr. Val Krukonis at AVCO in Lowell, Massachusetts, for the Office of Coal Research. In this method powdered coal is ejected into a hydrogen arc. The reactions which take place produce an output gas comprising approximately 11% acetylene, 80% hydrogen, and a variety of minor constituents. The process is said to use only the high temperatures associated with the hydrogen plasmas.

The present invention takes advantage of chemical species of hydrogen which are found in hydrogen plasmas. In particular, $H_3^+$ is a metastable hydrogen molecule found in plasmas in the pressure regime of 10–100 mm of mercury. It has associated with it approximately 240 Kcal/mole thermodynamic energy more than the $H_2$ molecule. It also has a charge associated with it. Because of the thermodynamic energy, reactions can be made to occur at lower temperatures than would be possible with molecular $H_2$. Because of the charge associated with it, it is possible to utilize electric and magnetic fields to direct these species to the coal to be processed.

The ionic processes involved in producing metastable $H_3^+$ include the following reactions.

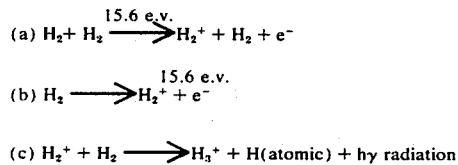

Thermodynamically, $H_3^+$ has associated with it 239.8 Kcal/mole, and H, atomic, has associated with it approximately 105 Kcal/mole. Because of the definition of thermodynamic free energy, these associated energies related to the active hydrogen species tend to promote reactions.

In the case of $H_3^+$ it is possible to use the Lorentz Force Concept $[\vec{F} = q(\vec{V} \times \vec{B} + \vec{\epsilon})]$ to direct the motion of the charged species in a manner to cause collisions with the materials to be processed.

Finally, the Gibbs magnetic free energy function and the Gibbs electric free energy function contribute to the thermodynamic considerations for a chemical reaction.

As a consequence of the fundamental considerations noted, favorable yields of various coal related products can be developed by adjusting the reaction thermodynamics electromagnetically in the presence of active hydrogen species.

SUMMARY OF THE INVENTION

Typical apparatus according to the present invention for reacting coal with hydrogen to provide hydrocarbon products comprises an anode and a cathode spaced therefrom in a container, means for applying to the anode an electric potential substantially more positive than the potential at the cathode to provide an electric arc in a reaction zone between the anode and the cathode comprising hydrogen at subatmospheric pressure and thus to maintain a plasma therein, means for providing a magnetic field approximately perpendicular to the arc, means for directing hydrogen into contact with the anode and from there into the reaction zone to ionize a substantial portion of the hydrogen positively, means for directing coal into contact with the cathode and from there into the reaction zone to charge a substantial portion of the coal negatively, means for reacting the materials as ionized whereby the free energy decreases for each reaction at a given temperature is greater than that for molecular hydrogen, and means for withdrawing the hydrocarbon products from the reaction zone.

Typically the anode has passages therethrough and the hydrogen directing means directs at least a substantial portion of the hydrogen through the passages into the reaction zone. Also typically the cathode has passages therethrough and the coal directing means directs at least a substantial portion of the coal through the passages into the reaction zone.

A typical method according to the present invention for reacting coal with hydrogen to provide hydrocarbon products comprises providing an anode and a cathode spaced therefrom in a container, applying to the anode an electric potential substantially more positive than the potential at the cathode to provide an electric arc in a reaction zone between the anode and the cathode comprising hydrogen at subatmospheric pressure and thus to maintain a plasma therein, providing a magnetic field approximately perpendicular to the arc, directing hydrogen into contact with the anode and from there into the reaction zone to ionize a substantial portion of the hydrogen positively, directing coal into contact with the cathode and from there into the reaction zone to charge a substantial portion of the coal negatively, reacting the materials as ionized whereby the free energy decrease for each reaction at a given temperature is greater than that for molecular hydrogen, and withdrawing the hydrocarbon products from the reaction zone.

Typically the anode has passages therethrough and at least a substantial portion of the hydrogen is directed through the passages into the reaction zone. Also typically the cathode has passages therethrough and at least a substantial portion of the coal is directed through the passages into the reaction zone. The coal may be directed into the reaction zone conveniently either in a slurry or as a fine powder.

The difference in potential between the anode and the cathode typically is about 200 to 1000 volts, the current density in the arc being maintained at about 0.01 to 100 amperes per square centimeter. Typically the pressure in the reaction zone is maintained at about 10 to 500 millimeters of mercury, and the magnetic field intensity is maintained at about 100 to 1000 gauss. The potential difference, current density, pressure, and magnetic field intensity typically are maintained at values such as to provide a temperature of about 500° to 6000° K in the reaction zone.

DESCRIPTION OF PREFERRED EMBODIMENTS

Figure 1:
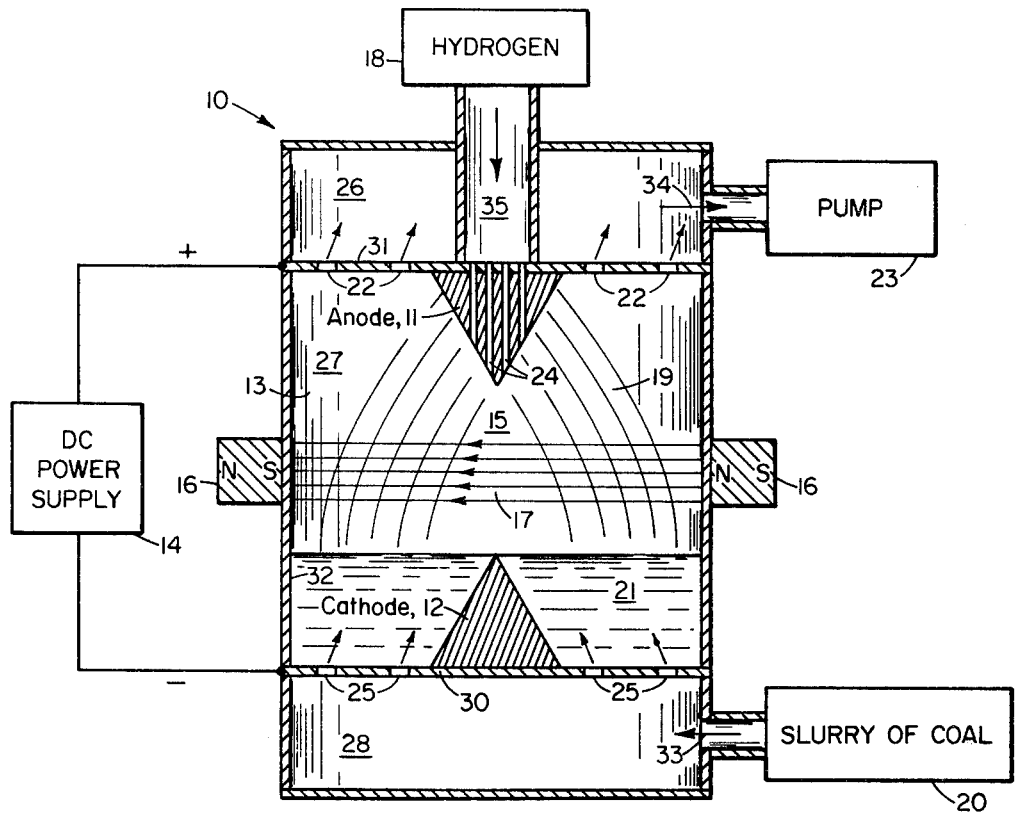
FIG. 1 is a schematic sectional view of typical apparatus according to the present invention.

Referring now to FIG. 1, typical apparatus 10 according to the present invention for reacting coal with hydrogen to provide hydrocarbon products comprises an anode 11 and a cathode 12 spaced therefrom in a container 13, means such as a power supply 14 for applying to the anode 11 an electric potential substantially more positive than the potential at the cathode 12 to provide an electric arc in a reaction zone at 15 between the anode 11 and the cathode 12 comprising hydrogen at subatmospheric pressure and thus to maintain a plasma 19 therein, means such as a magnet 16 for providing a magnetic field, as indicated at 17, approximately perpendicular to the arc, means 18 for directing hydrogen into contact with the anode 11 and from there into the reaction zone 15 to ionize a substantial portion of the hydrogen positively, means 20 for directing coal 21 into contact with the cathode 12 and from there into the reaction zone 15 to charge a substantial portion of the coal 21 negatively, means 14, 16, 23 for reacting the materials as ionized whereby the free energy decrease for each reaction at a given temperature is greater than that for molecular hydrogen, and means such as a pump 23 for withdrawing the hydrocarbon products from the reaction zone 15 through passages 22 and an outlet 34.

Typically the anode 11 has passages 24 therethrough and the hydrogen directing means 18 directs at least a substantial portion of the hydrogen through the passages 24 into the reaction zone 15. Also typically the cathode 12, 30 has passages 25 therethrough and the coal directing means 20 directs at least a substantial portion of the coal 21 through the passages 25 into the reaction zone 15.

A typical method according to the present invention for reacting coal with hydrogen to provide hydrocarbon products comprises providing an anode 11 and a cathode 12 spaced therefrom in a container 13, applying to the anode 11 an electric potential substantially more positive than the potential at the cathode 12 to provide an electric arc in a reaction zone at 15 between the anode 11 and the cathode 12 comprising hydrogen at subatmospheric pressure and thus to maintain a plasma 19 therein, providing a magnetic field, as indicated at 17, approximately perpendicular to the arc, directing hydrogen into contact with the anode 11 and from there into the reaction zone 15 to ionize a substantial portion of the hydrogen positively, directing coal 21 into contact with the cathode 12 and from there into the reaction zone 15 to charge a substantial portion of the coal 21 negatively, reacting the materials as ionized whereby the free energy decrease for each reaction at a given temperature is greater than that for molecular hydrogen, and withdrawing the hydrocarbon products from the reaction zone 15.

Typically the anode 11 has passages 24 therethrough and at least a substantial portion of the hydrogen is directed through the passages 24 into the reaction zone 15. Also typically the cathode 12 has passages 25 therethrough and at least a substantial portion of the coal 21 is directed through the passages 25 into the reaction zone 15. The coal may be directed into the reaction zone 15 conveniently either in a slurry or as a fine powder.

The difference in potential between the anode 11 and the cathode 12 typically is about 200 to 1000 volts, the current density in the arc being maintained at about 0.01 to 100 amperes per square centimeter. Typically the pressure in the reaction zone 15 is maintained at about 10 to 500 millimeters of mercury, and the magnetic field intensity at 17 is maintained at about 100 to 1000 gauss. The potential difference, current density, pressure, and magnetic field intensity typically are maintained at values such as to provide a temperature of about 500° to 6000° K in the reaction zone 15.

In typical apparatus 10 according to this invention, the vacuum-type container 13 is divided into compartments 26, 27, 28 by a cathode plate 30 and an anode plate 31 which are separated by an electrically and thermally insulating wall 32. The cathode plate 30 is connected electrically to the main portion of the cathode 12, which is conical in shape. The anode plate 31 is connected electrically to the main portion of the anode 11, which is conical in shape and has holes 24 in it for injection of hydrogen. Beneath the cathode 12 is an inlet 33 for the injection of the slurry of coal 20. The holes 25 in the cathode plate 30 allow the coal slurry to go into the plasma zone 15. Above the anode plate 31 is a port 34 leading to the pump 23 to maintain the desired low pressure in the chamber 13. The holes 22 through the anode plate 31 allow the passage of gas from the plasma zone 15 to the upper compartment 26 and out through the port 34 to the pump 23. The hydrogen supply 18 furnishes hydrogen through a pipe 35 and the passages 24 in the anode 11 into the reaction zone 15. The hydrogen is preheated by the anode 11 while flowing through the passages 24 therein, and thus also cools the anode 11. The magnets 16 are placed to provide a field of about 100 to 1,000 gauss surrounding and perpendicular to the current flow between the cathode 12 and the anode 11. The DC power supply 14 can furnish as much as 1,000 volts and 100,000 amperes to the cathode and anode.

A low-pressure arc discharge is formed between the anode 11 and the cathode 12, producing ionized species of hydrogen gas which are attracted to the cathode 12. The cathode 12 is in direct contact with the slurry of coal and furnishes a negative potential to the coal to cause the ionized species of hydrogen to be attracted to the coal. The applied magnetic field 17 serves to intensify the amount of ionization. It also acts upon diamagnetic organic products produced such as methane, ethane, ethylene, propene, acetylene, and other olefins to expel them from the reaction zone and thus to quench the product materials faster. The ions react with the coal to form gaseous species which are pumped out of the chamber 27 through the exit ports 22 in the anode plate or screen 31. The coal slurry is supplied through the entrance ports 25 in the cathode base plate or screen 30.

Figure 2:
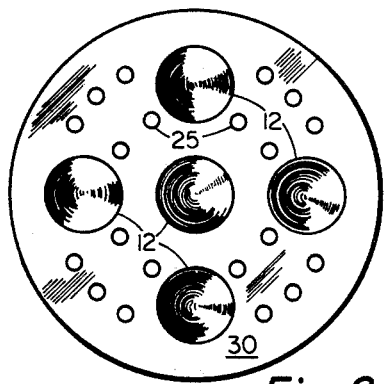
FIG. 2 is a plan view of a typical cathode for apparatus as in FIG. 1.
Figure 3:
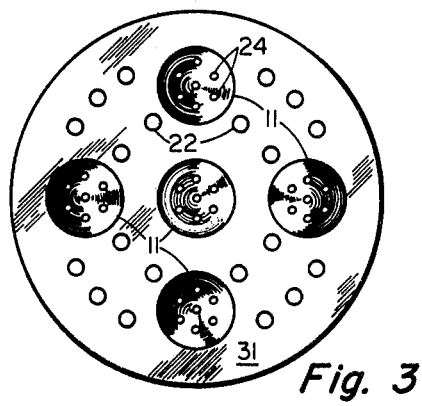
FIG. 3 is a plan view of a typical anode for apparatus as in FIG. 1.

For convenience, FIG. 1 shows the anode 11 and the cathode 12 each as a single conical member. For large volume processing of coal a plurality of oppositely disposed pairs of conical anode members 11 and cathode members 12 are needed, as shown in FIGS. 2 and 3.

Suitable materials for the anode 11 include stainless steel, tungsten, molybdenum, and copper coated with stainless steel, tungsten, or molybdenum. The anode support member 31 may comprise a screen or plate having passages 22 therethrough made of any strong conductive material. It is welded or in any other suitable way securely bonded in good electrical connection to the conical member 11 (or a plurality of the conical members 11, as in FIG. 3) and may be considered as a part of the anode 11. Similarly, suitable materials for the cathode 12 include stainless steel, tungsten, molybdenum, and copper coated with stainless steel, tungsten, or molybdenum. The cathode support member 30 may comprise a screen or plate having passages 25 therethrough made of any strong conductive material. It is welded or in any other suitable way securely bonded in good electrical connection to the conical member 12 (or a plurality of the conical members 12 as in FIG. 2) and may be considered as a part of the cathode 12. For convenience, the cathode 12 may in fact be identical with the anode 11 including the passages 24 through the conical member, which may serve as additional inlets for the coal slurry or powdered coal 21 into the reaction chamber 27.

The top and bottom portions 26, 28 of the container 13 may be made of steel or any other convenient materials that are strong enough for the purpose. The middle portion 32 of the container 13 may be made of quartz, coated metal, alumina, zirconia, ceramic plaster, or any other suitable high density material having good thermal and electrical insulating properties and sufficiently strong mechanically.

The container 13 typically has the shape of a right circular cylinder about 2 to 20 inches in diameter, about 4 to 30 inches in height, and with a spacing of about ¼ to 4 inches between the conical tips of the anode 11 and the cathode 12.

The magnet 16 may comprise one or more bar magnets or horseshoe magnets, and typically are of the electromagnet type for convenience in varying the magnetic intensity to control the reactions to be carried out. The magnetic field 17 preferably is located so as to surround the plasma 19, for maximum effectiveness. (The lines 19 also represent schematically the electric field in the reaction zone 15.)

Any convenient source of hydrogen 18 may be used, such as a storage container or electrolysis apparatus making available hydrogen at a regulated pressure of about 1 to 50 psia.

The coal feeding means 20 may comprise an auger screw, a pump, or other conventional means for supplying a slurry of coal or powdered coal to the inlet 33 of the container 13. The product withdrawing means 23 typically comprises a water evactor pump or other suitable pump for providing the desired partial vacuum.

In the low-pressure arc discharge there exist ions of $H_2^+$ and $H_3^+$ along with atomic hydrogen. The thermodynamic energy associated with these species is 360 kilocalories per mole for $H_2^+$, 240 kilocalories per mole for $H_3^+$ and 105 kilocalories per mole for atomic hydrogen. In a balance of free energy equations these thermodynamic energies will allow reactions to occur at temperatures below these required for molecular hydrogen. As a result, certain compounds such as methane, ethane, ethylene, propene, acetylene, and other olefins can be formed near temperatures where they remain stable thereby increasing the yield for these compounds. The charge associated with the $H_2^+$ and $H_3^+$ species allows them to be directed electromagnetically to the coal to be reacted.

Many reactions take place in the hydrogen plasma coal gasification processing. Some specific carbon-hydrogen reactions include:

$$4e^- + 3C + 4H_3^+ \rightarrow 3CH_4$$
$$2e^- + 6C + 2H_3^+ \rightarrow 3C_2H_2$$
$$4e^- + 6C + 4H_3^+ \rightarrow 3C_2H_4$$
$$2e^- + 2C + 2H_3^+ \rightarrow C_2H_6$$

A complete list of hydrocarbons would include longer chain hydrocarbons. However, in the reacting plasma, the major fraction of the hydrocarbons formed usually are the short chain molecules.

An example of the thermodynamic advantage of using the $H_3^+$ radical is obtained considering ethylene.
For ethylene:

$$\Delta G = \Delta H - T \Delta S$$

where $\Delta G$ is the free energy;

$\Delta H$ is the enthalpy;

T is absolute temperature;
$\Delta S$ is the entropy;
at 1000° K $$2C + 2H_2 \rightarrow C_2H_4$$

$$\Delta F \approx 28 \text{ Kcal/mole}$$

so the material formed is not stable, having a positive free energy of formation, however, $$2e^- + 6C + 2H_3^+(480 \text{ Kcal}) \rightarrow 3C_2H_2(84 \text{ Kcal})$$

$$\Delta G = -480 \text{ Kcal} + 84 \text{ Kcal}$$

$$\Delta G = -396 \text{ Kcal}$$

This is a very favorable reaction.

Similar advantages can be shown for a wide variety of reactions.

$$\Delta G \alpha - \vec{B} \cdot \vec{\Delta H} - \vec{D} \cdot \vec{\Delta \epsilon}$$

Therefore, increases in magnetic field intensity and electric field intensity tend to lower the free energy of the system in the case of paramagnetic and ferromagnetic materials. However, generally these field variable contributions are small. In the case of diamagnetic materials, the magnetic term tends to increase the free energy. Since many organic molecules are diamagnetic, this contribution slightly decreases the reaction favorability from the viewpoint of free energy change. But the magnetic field causes a net favorable result because of its effect on the plasma.

Figure 4:
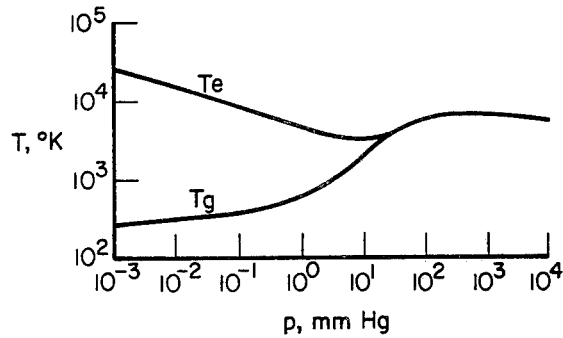
FIG. 4 is a plasma temperature diagram for a particular discharge current density illustrating features of the present invention.

The temperature of the gas in a plasma can be controlled under a given set of discharge current, discharge voltage, and magnetic field conditions, by varying the background gas pressure. FIG. 4 shows how the gas temperature (related to specific enthalpy of the gas) and the electron temperature (related to the average kinetic energy of the electrons) vary with gas pressure in a low pressure arc discharge as in the present invention.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A method of reacting coal with hydrogen to provide hydrocarbon products that comprises
    providing an anode and a cathode spaced therefrom in a container,
    applying to the anode an electric potential substantially more positive than the potential at the cathode to provide an electric arc in a reaction zone between the anode and the cathode comprising hydrogen at subatmospheric pressure and thus to maintain a plasma therein,
    providing a magnetic field of at least about 100 gauss approximately perpendicular to the arc,
    directing hydrogen into contact with the anode and from there into the reaction zone to ionize a substantial portion of the hydrogen positively,
    directing coal into contact with the cathode and from there into the reaction zone to charge a substantial portion of the coal negatively,
    reacting the materials as ionized whereby the free energy decrease for each reaction at a given temperature is greater than that for molecular hydrogen, and
    withdrawing the hydrocarbon products from the reaction zone.

2. A method as in claim 1, wherein the anode has passages therethrough and at least a substantial portion of the hydrogen is directed through the passages into the reaction zone.

3. A method as in claim 1, wherein the cathode has passages therethrough and at least a substantial portion of the coal is directed through the passages into the reaction zone.

4. A method as in claim 1, wherein the coal is directed into the reaction zone either in a slurry or as a fine powder.

5. A method as in claim 1, wherein the difference in potential between the anode and the cathode is about 200 to 1000 volts.

6. A method as in claim 1, wherein the current density in the arc is maintained at about 0.01 to 100 amperes per square centimeter.

7. A method as in claim 4, wherein the pressure in the reaction zone is maintained at about 10 to 500 millimeters of mercury.

8. A method as in claim 4, wherein the magnetic field intensity is maintained at about 100 to 1000 gauss.

9. A method as in claim 1, wherein the potential difference, current density, pressure, and magnetic field intensity are maintained at values such as to provide a temperature of about 500° to 6000° K in the reaction zone.

* * * * *